United States Patent [19]
Kierkels et al.

[11] Patent Number: 5,407,828
[45] Date of Patent: Apr. 18, 1995

[54] **PROCESS FOR STEREOSELECTION OF (2R,3S)-3-PHENYLGYCIDIC ESTER USING LIPASE FROM *CANDIDA ANTARCTICA***

[75] Inventors: Joannes G. T. Kierkels, Sittard; Wijnand P. H. Peeters, Maasbree, both of Netherlands

[73] Assignee: DSM N.V., Netherlands

[21] Appl. No.: 165,344

[22] Filed: Dec. 13, 1993

[30] Foreign Application Priority Data

Dec. 18, 1992 [NL] Netherlands ......................... 9202208

[51] Int. Cl.$^6$ ..................... C12P 41/00; C12N 1/16
[52] U.S. Cl. ................... 435/280; 435/255.4
[58] Field of Search .............................. 435/280, 255.4

[56] References Cited

U.S. PATENT DOCUMENTS

| | | | |
|---|---|---|---|
| 5,156,963 | 10/1992 | Eigtved | 435/135 |
| 5,169,779 | 12/1992 | Zard et al. | 435/280 |
| 5,273,898 | 12/1993 | Ishii | 435/198 |

FOREIGN PATENT DOCUMENTS

| | | |
|---|---|---|
| 343714 | 11/1989 | European Pat. Off. . |
| 362556 | 4/1990 | European Pat. Off. . |
| 417785 | 3/1991 | European Pat. Off. . |
| 9004643 | 5/1990 | WIPO . |

*Primary Examiner*—Douglas W. Robinson
*Assistant Examiner*—Sandra Saucier
*Attorney, Agent, or Firm*—Cushman Darby & Cushman

[57] ABSTRACT

The invention relates to the preparation of an optically active ester of trans-3-phenylglycidic acid in which a mixture of the 2 enantiomers of the trans-3-phenylglycidic acid ester is stereoselectively hydrolyzed using an enzyme originating from *Candida antarctica* and the non-hydrolyzed ester is separated off from the reaction mixture.

A racemic mixture of trans-phenylglycidic acid esters is selectively and enzymatically hydrolyzed in a relatively short reaction time, the residual ester being obtained in a high yield and with a high e.e. Such esters are used for the preparation of pharmaceuticals such as benzothiazepines and benzazepines.

10 Claims, No Drawings

PROCESS FOR STEREOSELECTION OF (2R,3S)-3-PHENYLGYCIDIC ESTER USING LIPASE FROM *CANDIDA ANTARCTICA*

The invention relates to a process for the preparation of an optically active ester of trans-3-phenyl-glycidic acid according to the general formula

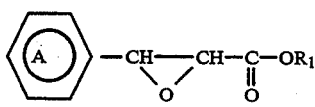

$R_1$ being a group derived from an alcohol, for instance a substituted or unsubstituted alkyl group; and A being an aromatic ring, for instance a phenyl ring, which may be substituted or unsubstituted, in which a mixture of two enantiomers of trans-3-phenylglycidic acid ester is stereoselectively hydrolyzed with an enzyme originating from the *Candida* genus and the nonhydrolyzed ester is separated off from the reaction mixture.

EP-A-362556 discloses the stereoselective enzymatic hydrolysis of racemic trans-methyl-3-(4-methoxyphenyl)glycidic acid ester using a large number of enzymes, including *Candida cylindracea*. Applicant has found that *Candida cylindracea* loses its activity and stereoselectivity at temperatures of 50° C. or higher.

WO-A-9004643, too, discloses the enzymatic hydrolysis of a racemic mixture of two enantiomers of trans-methyl-3-(4-methoxyphenyl)glycidic acid ester using a large number of enzymes, including an enzyme isolated from *Candida cylindracea*. From the description it is clear that the enzymatic hydrolysis using the *Candida cylindracea* enzyme usually gives a low e.e. (enantiomeric excess) while, in addition, the enzyme proves to be very sensitive to the solvent chosen.

There is a large need to find a suitable enzyme for the preparation of these chiral compounds. The object of the invention is to provide a process which does not have the above-mentioned drawbacks and in which a racemic mixture of trans-phenylglycidic acid esters is selectively and enzymatically hydrolyzed in a relatively short reaction time, in which process the residual ester can be obtained in a high yield and with a high e.e.

According to the invention this is achieved by using an enzyme originating from *Candida antarctica*.

The subject invention is based on enantioselective enzymatic hydrolysis of a mixture of two enantiomers of trans-3-phenylglycidic ester using an enzyme originating from *Candida antarctica*. It has been found that the enzymatic hydrolysis can be carried out stereoselectively at higher temperatures than demonstrated so far in literature, for instance at temperatures up to 80° C. As a result, the reaction time can be shortened substantially. Moreover, the enzyme seems to be less sensitive to the solvent chosen, which implies that good selectivities are achieved in different solvents.

The trans-3-phenylglycidic acid ester according to formula I can optionally contain one or more substituents on aromatic ring A, e.g. at the 4-position. The substituents may be chosen, for instance, from hydroxy, alkoxy with 1–6 C atoms, alkyl with 1–6 C atoms and halogen. The aromatic ring A can also be polycyclic. The group derived from an alcohol, $R_1$, being an ester residue, is mostly an alkyl group with 1–6 carbon atoms; preferably it is methyl, ethyl, isopropyl or isobutyl.

The enantiomeric excess, which is a measure of the enantiomeric purity and is usually denoted as 'e.e.', is a quantity often used. Briefly put, the enantiomeric excess is equal to the difference between the amounts of enantiomers divided by the sum of the amounts of enantiomers, which quotient can be expressed as a percentage after multiplication by 100.

The esters of trans-3-phenylglycidic acid of the formula I given above can be prepared for instance by Darzens-condensation or by epoxydation of esters of trans-cinnamic acid.

The esters of trans-3-phenylglycidic acid according to formula I have two chiral centres. Molecules with n chiral centres in principle have $2^n$ stereoisomers. For 3-phenyl-glycidic acid esters, therefore, 4 stereoisomers are conceivable, which occur as two D,L pairs, which are mutually diastereoisomers. The two diastereoisomeric forms of 3-phenylglycidic acid esters are the cis and the trans form. The two enantiomers in the trans form have (2R,3S) and (2S,3R) as configuration. The configurations of the cis form are (2R,3R) and (2S,3S), respectively. For the preparation of benzothiazepine and benzazepine mostly the enantiomer having the (2R,3S) configuration is applied.

The invention also relates to the use of the optically active ester as intermediate in the preparation of pharmaceuticals, for instance, benzothiazepine such as naltiazem, clentiazem and diltiazem, benzazepine and taxol.

Diltiazem is the commercial name of 2-(4′-methoxyphenyl)-3-acetyloxy-5-[2-(dimethylamino)ethyl]-2,3-dihydro-1,5-benzothiazepine-4-(5H)-on and is known, for instance, from US-A-3562257. Diltiazem is a calcium antagonist that is used for cardiovascular disorders such as angina pectoris. In addition, it is also applied in case of heart rate problems and against hypertension. If diltiazem is to be prepared, the trans-3-phenylglycidic acid ester contains a para-methoxyphenyl ring as A, while $R_1$ then is mostly a methyl group.

Enzymatic hydrolysis of racemic esters, such as applied for the subject invention for hydrolysis of trans-3-phenyl glycidate ester, is known. At 50% conversion a fully stereoselective enzyme yields both optically pure product and optically pure residual substrate. In practice, however, enzymes are not fully selective. If, therefore, it is desired in practice to obtain the product of an enantioselective enzymatic conversion with a high degree of enantiomeric purity, the conversion will preferably be terminated at less than 50%.

If, on the other hand, it is desired to obtain the residual substrate (in the present case the ester) with a high degree of enantiomeric purity, it will be preferred to continue the conversion up to a degree of conversion of more than 50%, until the desired enantiomeric excess is reached.

The selectivity and the efficiency of an enzymatic enantioselective conversion, in other words the enantioselectivity, will increase with the difference in conversion rate between the enantiomers. The difference in conversion rate in the presence of a certain enzyme can to a certain extent be influenced by a suitable choice of the process parameters. Naturally, it will be attempted to optimize the choice of the process parameters for the particular enzyme that is being used. One skilled in the art can simply determine these parameters on the basis of experiments designed for that purpose.

As described, for instance, in the publication by Ching-Shih Chen et al., J. Am. Chem. Soc. 104 (1982), 7294-7299, in most cases a higher enantiomeric purity can be realized in the residual substrate than in the product formed.

The enzyme used according to the subject invention is a lipase originating from *Candida antarctica*. This lipase can, for instance, be produced via recombinant DNA technology. The gene coding for the lipase in question is heterologously expressed in a host microorganism, for instance *Aspergillus oryzae*. This enzyme is commercially available e.g. from NOVO under the tradename SP 435 and SP 525.

Through the enzymatic hydrolysis of a trans-3-phenylglycidic acid ester with *Candida antarctica* lipase the (2S,3R) enantiomer of the trans-3-phenylglycidic acid ester is hydrolyzed with a high selectivity, so that the (2R,3S) enantiomer can be obtained with a high e.e.

The reaction velocities of the enantiomers appear to differ appreciably, so that, starting from a racemic mixture, at a conversion of less than 53% an enantiomeric excess of more than 95% of the (2R,3S)-3-(4-methoxyphenyl)glycidic ester enantiomer can already be obtained. An enantiomeric excess of more than 98% is already obtained, again starting from a racemic mixture, at a conversion of about 55%. When use is made of mixtures enriched with the target enantiomer, the results obtained are better, while the enzyme retains its selectivity.

The enzyme according to the invention is preferably applied in its immobilized form, i.e. on a solid phase, inter alia on microporous particles, gel-type particles and ion exchange resins. This facilitates recovery of the enzyme, while enabling reuse of the enzyme. It has been found that a high activity and selectivity are reached also when the enzyme is used in immobilized form, said activity and selectivity being retained after the enzyme had been recycled several times.

The stereoselective hydrolysis is preferably effected in a two-phase system comprising an aqueous phase and an organic phase containing an organic solvent. Examples of such a solvent are solvents that are not or only to a small extent soluble in water, such as chloroform, isopropyl ether, 3-pentanone, dichloro methane, trichloro ethane, benzene, toluene, xylene, methyl t-butyl ether, methyl isobutyl ketone, cyclohexanone, isooctane, ethyl acetate and others. Surprisingly, the selectivity of the enzyme according to the invention is almost independent of the solvent chosen, it being possible in most cases to achieve an e.e. higher than 95% at a conversion below 53%. The hydrolysis according to the invention can be carried out at room temperature or at elevated temperature. The upper limit is determined by the stability of the substrate and in practice is about 80° C. Preferably, a temperature of 20°-60° C. is used, in particular 30°-50° C. The use of higher temperatures has the advantage that the reaction proceeds faster.

During the hydrolysis the pH is kept at a value of 5 to 10, preferably 7-9, and in particular at about 8, for instance by addition of a base. The residual ester, i.e. the enantiomer that has not been hydrolyzed, can for instance be recovered by separation of the organic solvent in which the ester is dissolved, followed by recovery of the ester from the solution.

According to the subject invention the optically active ester of (2R,3S)-3-(4-alkoxyphenyl)glycidic acid, preferably (2R,3S)-3-(4-methoxyphenyl)glycidic acid, is obtained with an e.e. higher than 95%, preferably higher than 98%.

The invention will be elucidated on the basis of the examples, without being limited thereto.

The enantiomeric excess (e.e.) of the (2R, 3S) ester was determined via HPLC analysis using a chiracel OD column (Daicel Chemical Industries Ltd; solvent: hexane/isopropanol=70/30).

EXAMPLE I 20 g of racemic trans-methyl-3-(4-methoxyphenyl)glycidate was dissolved in 180 ml of methyl isobutyl ketone, after which 180 ml of 50 mM Tris (tris(hydroxymethyl)aminomethane)/HCl buffer, pH 8, was added. After addition of 100 mg of *Candida antarctica* lipase (SP 525) the pH was kept constant at 8 by means of automatic titration with 2N aqueous NaOH. The temperature was kept at 30° C. Analysis of the reaction mixture after 7.5 hours' hydrolysis revealed an enantiomeric excess of the (2R,3S) ester of 97%.

EXAMPLE II

After dissolution of 10 g of racemic trans-methyl-3-(4-methoxyphenyl)glycidate in 75 ml of toluene and addition of 75 ml of 50 mM potassium phosphate buffer having a pH of 7,200 mg of *Candida antarctica* lipase (SP 525) was added. After 3 hours' reacting at 30° C., the pH being kept constant by means of titration with 2N NaOH, an enantiomeric excess of 99% was measured.

EXAMPLE III

Example II was repeated, now the pH being kept constant at 8. After 2 hours' reacting an enantiomeric excess of 97% was measured.

EXAMPLE IV

Example II was repeated, the reaction now being carried out at 50° C. After hydrolysis had taken place for 1 hour, an enantiomeric excess of 97% was measured.

EXAMPLE V

With stirring, 20 g of racemic trans-methyl-3-(4-methoxyphenyl)glycidate was added to 60 ml of organic solvent, as stated in Table 1. Then 60 ml of 50 mM Tris/HCl buffer, of pH 8, was added. After addition of 2 g of immobilized *Candida antarctica* lipase (SP 435) the pH was kept constant at 8 by means of automatic titration with 2N NaOH. The reaction was carried out at 30° C.

The results are presented in Table 1.

TABLE 1

| organic solvent | time (min) | e.e. (%) |
| --- | --- | --- |
| methyl t-butyl ether | 250 | 99 |
| ethyl acetate | 400 | 93 |
| cyclohexanone | 500 | 97 |
| methyl isobutyl ketone | 370 | 99 |
| isooctane | 500 | 85 |
| 3-pentanone | 500 | 97 |
| isopropyl ether | 240 | 96 |

EXAMPLE VI 20 g of racemic trans-methyl-3-(4-methoxyphenyl)glycidate was dissolved in 60 ml of methyl isobutyl ketone. This was followed by addition of 60 ml of 50 mM Tris/HCl buffer of pH 8. After addition of 4 g of immobilized *Candida antarctica* lipase (SP 435) the pH was kept constant at 8 by means of automatic titration with 2N NaoH. The hydrolysis was carried out at 30° C.

After 5 hours the reaction was stopped by filtration of the reaction mixture, the biocatalyst remaining behind as residue. The biocatalyst was washed with 2×40 ml of methyl isobutyl ketone. After the aqueous phase had been separated off, the collected organic phase was twice washed with 30 ml of 20% sodium bisulphite solution, and then with 2×20 ml of 5% sodium bicarbonate solution. The organic phase was dried over MgSO$_4$ and evaporated. Via crystallization in methanol (MeOH) 7.5 g of (2R,3S)-3-(4-methoxyphenyl)glycidate ester was obtained.

$[\alpha]_D^{20} = -203°$ (C=1 MeOH). Melting point 84°-87° C.

EXAMPLE VII

Example VI was repeated, the recovered immobilized biocatalyst from Example VI being reused under the same conditions. After 6 hours' hydrolysis the trans (2R,3S) ester was isolated as described in Example VI. 7.0 g of (2R,3S)-3-(4-methoxyphenyl)glycidate ester was obtained $[\alpha]_D^{20} = -204°$ (c=1 MeOH). Melting point 84°-87° C.

EXAMPLE VIII

Example VI was repeated, now use being made of 2 g of *Candida antarctica* lipase (SP 435). The enantiomeric excess of the (2R,3S) ester, measured after 6 hours' hydrolysis, was 99%.

EXAMPLE IX 10 g of racemic trans-methyl-3-(-4-methoxyphenyl)-glycidate was dissolved in 60 ml of methyl t-butyl ether, following which 60 ml of 50 mM Tris/HCl buffer of pH 8 was added. Subsequently, 4 g of immobilized *Candida antarctica* lipase (SP 435) was added and the pH was kept constant at 8 by means of automatic titration with 2N NaOH. The hydrolysis was carried out at 60° C.

After 3 hours' hydrolysis an enantiomeric excess of 90% was measured for the (2R,3S) ester.

EXAMPLE X 5 g of racemic trans-methyl-3-(4-methoxyphenyl)-glycidate was dissolved in 60 ml of isooctane, following which 60 ml of 50 mM Tris/HCl buffer of pH 8 was added. After addition of 2 g of immobilized *Candida antarctica* lipase (SP 435) the pH was kept constant at 8 by means of automatic titration with 2N NaOH. The hydrolysis was carried out at 80° C.

After 150 minutes' hydrolysis an enantiomeric excess of 95% was measured.

EXAMPLE XI 1.5 g of racemic trans-methyl-3-(4-methoxyphenyl)-glycidate was dissolved in 60 ml of chloroform, following which 60 ml of 50 mM Tris/HCl buffer of pH 8 was added. After addition of 4 g of immobilized *Candida antarctica* lipase (SP 435) the pH was kept constant at 8 by means of automatic titration with 2N NaOH. The hydrolysis was carried out at 50° C.

After 240 minutes the enantiomeric excess of the (2R,3S) ester was 96%.

We claim:

1. A process for the preparation of an optically active (2R,3S) ester of trans-3-phenyl-glycidic acid having the general formula

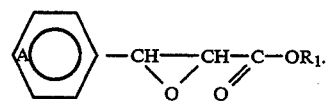

wherein said formula R$_1$ is a group derived from an alcohol, A represents an aromatic ring, which process comprises allowing an enzyme of *Candida antarctica* to act on a mixture of the enantiomers of trans-3-phenylglycidic ester to stereolectively hydrolyze one of said enantiomers wherein the non-hydrolyzed enantiomer has the (2R,3S) configuration, and separating said non-hydrolyzed enantiomer from the mixture.

2. A process according to claim 1, wherein the non-hydrolyzed ester is the methyl ester of (2R,3S)-3-(4-methoxyphenyl)-glycidic acid.

3. A process according to claim 1, wherein the stereoselective hydrolysis is conducted at a temperature greater than 30° C.

4. A process according to claim 1, wherein said stereoselective hydrolysis is conducted in a two phase system of water and organic solvent, wherein said organic solvent is insoluble or only soluble to a small extent in water.

5. A process according to claim 4, wherein said organic solvent is selected from the group consisting of chloroform, methyl isobutyl ketone, ethyl acetate, 3-pentenyl, cyclohexane, isooctane, isopropyl ether, methyl t-butyl ether, dichloro methane, trichloro methane, benzene, toluene and xylene.

6. A process according to claim 1, wherein the enzyme is immobilized.

7. A process according to claim 1, wherein the optically active ester of (2R, 3S)-3-phenyl glycidic acid is obtained in an enantiomeric excess greater then 98%.

8. A process according to claim 1, wherein said process further comprises preparing benz(othi)azepines from the separated (2R,3S) ester of trans-3-phenylglycidic acid.

9. A process according to claim 8, wherein said process further comprises subjecting said separated ester to a coupling reaction with thiophenol and alkylating or acylating the product obtained from the coupling reaction.

10. A process according to claim 2, wherein that process further comprises preparing 2-(4'-methoxyphenyl)-3-acetyloxy-5-[2-(dimethylamino)ethyl]-2,3-dihydro-1,5-benzothiazepine-4-(5H)-one from said non-hydrolyzed ester.

* * * * *